United States Patent [19]
Cho et al.

[11] Patent Number: 5,451,221
[45] Date of Patent: Sep. 19, 1995

[54] ENDOSCOPIC LIGHT DELIVERY SYSTEM

[75] Inventors: George Cho, Hopkinton; Horace W. Furumoto, Wellesley; James Boll, Jamaica Plain, all of Mass.

[73] Assignee: Cynosure, Inc., Bedford, Mass.

[21] Appl. No.: 174,272

[22] Filed: Dec. 27, 1993

[51] Int. Cl.⁶ ............................................. A61N 5/06
[52] U.S. Cl. .......................................... 606/3; 606/14; 606/15; 606/7
[58] Field of Search ................................ 606/7, 14–17, 606/3

[56] References Cited

U.S. PATENT DOCUMENTS

| | | |
|---|---|---|
| 4,592,353 | 6/1986 | Daikuzono . |
| 4,740,047 | 4/1988 | Abe et al. . |
| 4,773,413 | 9/1988 | Hussein et al. . |
| 4,860,743 | 8/1989 | Abela . |
| 4,887,600 | 12/1989 | Watson et al. . |
| 4,913,142 | 4/1990 | Kittrell et al. . |
| 4,955,882 | 9/1990 | Hakky . |
| 5,011,483 | 4/1991 | Sleister . |
| 5,061,266 | 10/1991 | Hakky . |
| 5,066,292 | 11/1991 | Müller et al. ............................ 606/7 |
| 5,147,353 | 9/1992 | Everett . |
| 5,151,097 | 9/1992 | Diakuzono ....................... 606/17 X |
| 5,163,935 | 11/1992 | Black et al. . |
| 5,201,731 | 4/1993 | Hakky . |
| 5,207,672 | 5/1993 | Roth et al. . |
| 5,242,437 | 9/1993 | Everett et al. . |
| 5,242,438 | 9/1993 | Saadatmanesh et al. ............. 606/15 |
| 5,267,995 | 12/1993 | Doiron et al. ........................ 606/15 |
| 5,292,320 | 3/1994 | Brown et al. ...................... 606/17 X |
| 5,304,167 | 4/1994 | Freiberg ............................ 606/15 X |
| 5,354,294 | 10/1994 | Chou ..................................... 606/16 |
| 5,366,456 | 11/1994 | Rink et al. ........................... 606/16 |

FOREIGN PATENT DOCUMENTS

| | | | |
|---|---|---|---|
| 2826383 | 12/1979 | Germany . | |
| WO06727 | 6/1990 | Japan .................................... 606/17 |

OTHER PUBLICATIONS

McNicholas, T. A., et al., "Intersitial Laser Coagulation of the Prostate: Experimental Studies," SPIE, 1421:30–35 (1991). (From *Proceedings of Lasers in Urol., Laparoscopy, and General Surgery*, Jan. 21≧23, 1991).

Moretti, Michael, "Lasers Improve Prostatectomy Treatment," Medical Laser Buyers Guide, 94–96 (1992).

Moretti, Michael, "Holmium Boosts Orthopedic Laser Development," Medical Laser Buyers Guide, p. 93 (1992).

Costello, Anthony J., et al., "Nd:YAG Laser Ablation of the Prostate as a Treatment for Benign Prostatic Hypertrophy," *Lasers in Surgery and Medicine*, 12:121–124 (1992).

Kandel, Laurence B., M.D., et al., "Transurethal Laser Prostatectomy in the Canine Model," *Lasers in Surgery and Medicine*, 12:33–42 (1992).

McCullough, David L., M.D., "Transurethal Laser Treatment of Benign Prostatic Hyperplasia," and Transurethal Ultrasound–guided Laser–Induced Prostatectomy (Tulip Procedure): A Canine Prostate Feasibility Study, by Roth, A. M.D., et al., *The Journal of Urology*, 146:1126–1135 (1991).

"The Laser TURP Advantage," Intra–Sonix, Inc. pp. 1–4 (1991).

"Lasers Battle for Prostatectomy Market," Medical Laser Industry Report, 5:1–3 (Aug., 1991).

Watson, G. M., MS, "Minimally Invasive Therapies of the Prostate," *Minimally Invasive Therapy*, 1:231–240 (1992).

U.S. Patent application Ser. No. 08/049,136 filed on Apr. 19, 1993 by Krishna M. Bhatta entitled "Surgical Device and Method," Group Art Unit 3309 (copy not submitted).

*Primary Examiner*—Peter A. Aschenbrenner
*Attorney, Agent, or Firm*—Hamilton, Brook, Smith & Reynolds

[57] ABSTRACT

An endoscopic light delivery system for delivering light to tissue includes a laser source for generating light. Fiber optics are optically coupled to the laser source for conveying the light generated by the laser source. A focusing surface is formed at an end of the fiber optics. The focusing surface of the fiber optics is shaped for redirecting light conveyed by the fiber optics in a direction lateral to the fiber optics for cutting tissue. A single optical fiber or a bundle of optical fiber can be used to transmit plural wavelengths of light for aiming cutting and coagulating.

15 Claims, 3 Drawing Sheets

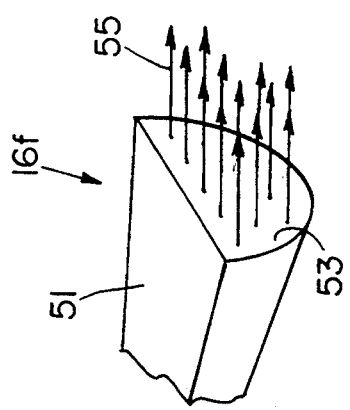
FIG. 5B
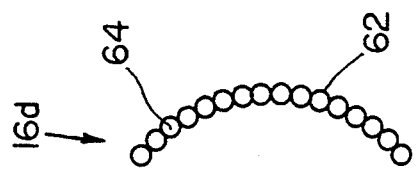
FIG. 7
FIG. 5A
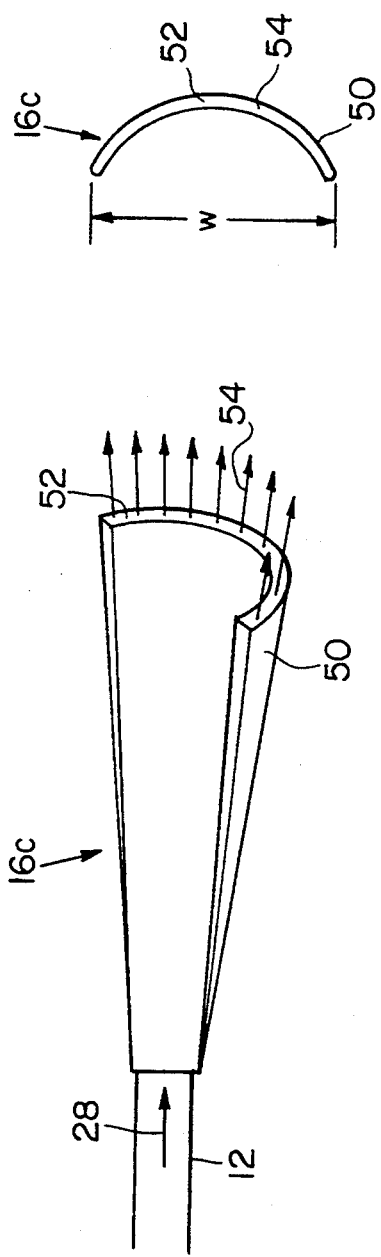
FIG. 4
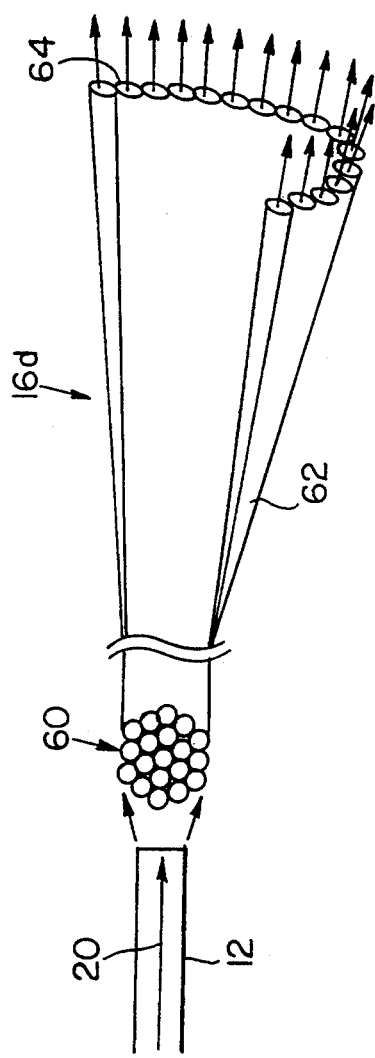
FIG. 6

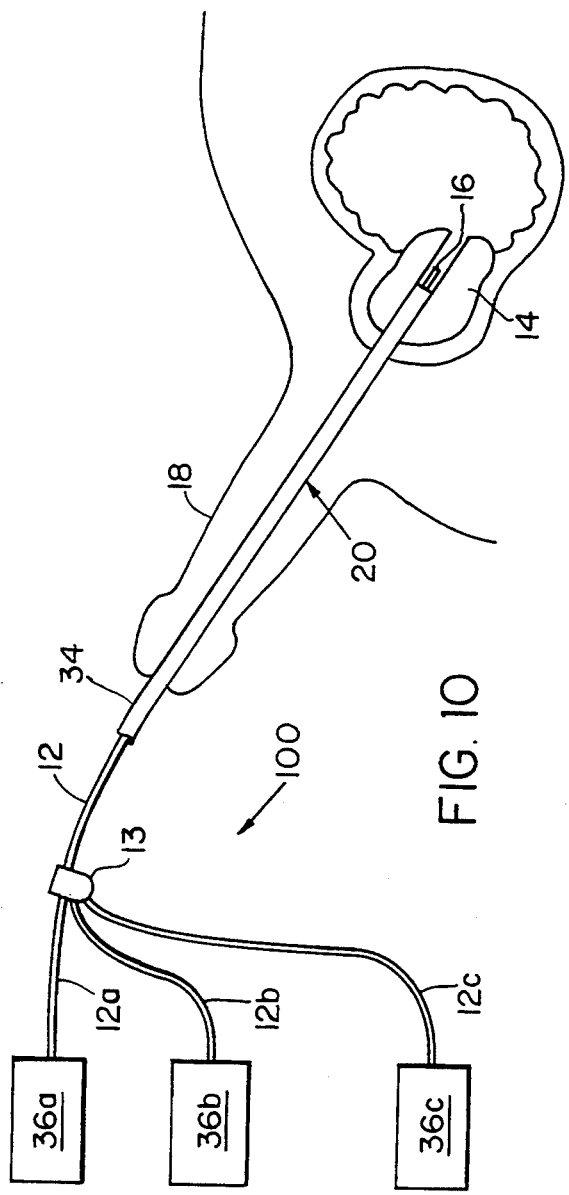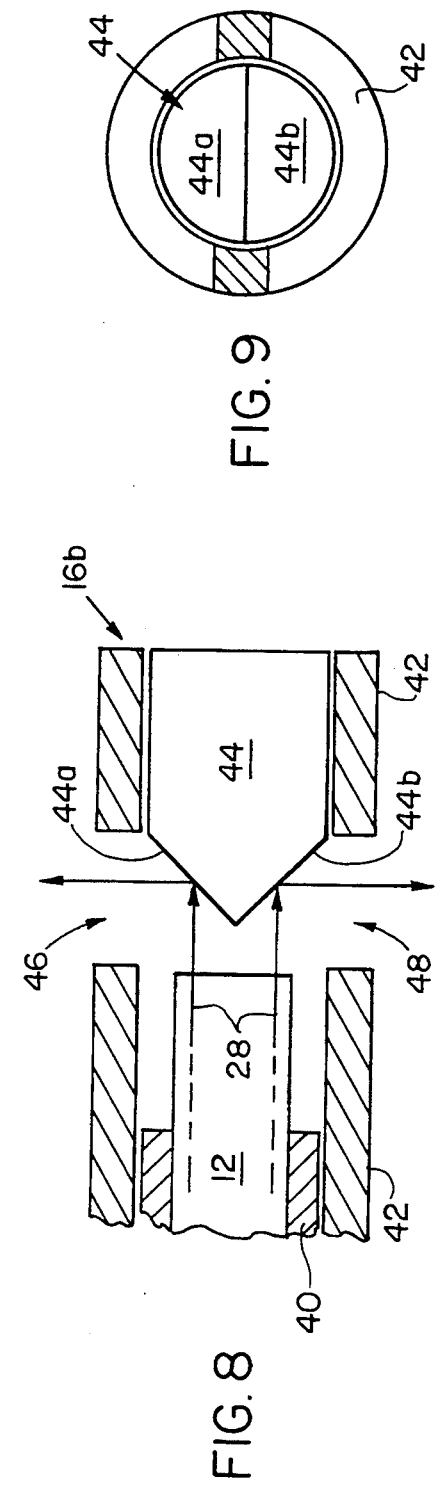

ENDOSCOPIC LIGHT DELIVERY SYSTEM

BACKGROUND

Endoscopic surgery is often used to perform prostate, intra-uterine, bladder and urinary track surgery. The most common method of performing prostate surgery is to resect the enlarged prostate gland with an electrosurgical loop inserted into the urethra through an endoscope. The electrosurgical device shaves off small pieces of prostate tissue in order to enlarge the passageway, thereby providing the patient with relief. A problem with this method of surgery is that substantial bleeding occurs as the prostate tissue is being cut, making visibility through the endoscope difficult. Blood loss also complicates the surgical operation and lengthens the hospital stay. Additionally, this method of surgery is difficult to perform making extensive training necessary. Finally, the procedure is lengthy, taking up to 1½ hours to perform.

Another method of performing prostate surgery is to insert an optical fiber which is optically coupled to a laser into the prostate gland through an endoscope. The laser energy conveyed by the optical fiber coagulates or cooks surrounding prostate gland tissue. In some instances, it is desirable for the optical fiber to include a tip which directs the laser energy laterally in order to make the procedure easier to perform. The coagulated tissue remains in place for about four to six weeks before the coagulated tissue falls off and is passed during urination. Therefore, the patient must endure a long period of discomfort and may need a catheter for passage of urine until the coagulated tissue is finally passed.

An attempt to alleviate the problems of both procedures is disclosed in U.S. Pat. No. 5,011,483, issued to Sleister, where a laser/electrosurgical instrument provides laser energy for coagulating tissue and an electrosurgical loop for cutting the coagulated tissue. The coagulation of the tissue prevents bleeding when the tissue is cut away.

SUMMARY OF THE INVENTION

The problem with the approach of the Sleister patent is that both an electrocautery device and a laser are employed. Accordingly, there is a need for a procedure for performing prostate surgery which provides immediate relief without substantial bleeding and which does not require both a laser and an electrocautery device.

In accordance with the present invention, prostate tissue can be cut and coagulated with laser technology without employing an electrocautery device. The present invention provides an endoscopic light delivery system primarily for cutting tissue including fiber optics for conveying light. A focusing surface is formed at an end of the fiber optics. The focusing surface of the fiber optics is shaped for redirecting light conveyed by the fiber optics in a direction lateral to the fiber optics. In preferred embodiments, the focusing surface of the fiber optics is coated with a reflective coating for reflecting light.

In another preferred embodiment of the present invention, an endoscopic light delivery system principally for cutting tissue includes a laser source for generating light. Fiber optics optically coupled to the laser convey light generated by the laser. A tip member is optically coupled to the fiber optics. The tip member is shaped in an arch to direct the conveyed light into an arch-shape profile similar to a curved tip chisel.

In another preferred embodiment of the present invention, an endoscopic light delivery system primarily for coagulating tissue includes fiber optics for conveying light. A mirror is positioned proximate to an end of the fiber optics. The mirror is shaped for redirecting light conveyed by the fiber optics in plural lateral directions with respect to the fiber optics. A sheath surrounds the fiber optics and mirror for positioning the fiber optics and mirror with respect to each other.

In another preferred embodiment, the present invention provides a laser light delivery system for simultaneously cutting and coagulating tissue including a first laser source for generating light of a first wavelength for cutting tissue. A second laser source generates light of a second wavelength for coagulating tissue. A third laser source generates light for targeting tissue. Fiber optics are optically coupled to the first, second and third laser sources for simultaneously conveying the light generated by the first, second and third laser sources. A light delivery tip optically coupled to the fiber optics delivers the light conveyed by the fiber optics. As a result, the same device can be used to cut and coagulate tissue making the procedure faster and simpler than previous methods of prostate surgery. In preferred embodiments, the light generated by the first laser source has a wavelength ranging from about 1.4 to 2.1 microns while the light generated by the second laser source has a wavelength of approximately 0.8 to 1.1 microns.

The present invention light delivery system provides a method for performing prostate surgery in which tissue is cut and cauterized speedily using the same quartz optical fiber without employing an electrocautery device, thereby minimizing bleeding and providing the patient with immediate relief.

BRIEF DESCRIPTION OF THE DRAWINGS

The foregoing and other objects, features and advantages of the invention will be apparent from the following more particular description of preferred embodiments of the drawings in which like reference characters refer to the same parts throughout the different views. The drawings are not necessarily to scale, emphasis instead being placed upon illustrating the principles of the invention.

FIG. 4 is a perspective view of another preferred light delivery tip.

FIG. 5A is an end view of the light delivery tip depicted in FIG. 4.

FIG. 5B is a perspective view of another preferred light delivery tip.

FIG. 6 is a perspective view of still another preferred light delivery tip.

FIG. 7 is an end view of the light delivery tip depicted in FIG. 6.

FIG. 8 is a side view of another preferred light delivery tip.

FIG. 9 is a sectional view of the light delivery tip of FIG. 8 showing the mirror.

FIG. 10 is a simplified view of another preferred endoscopic light delivery system.

DETAILED DESCRIPTION OF THE PREFERRED EMBODIMENTS

Figure 1:
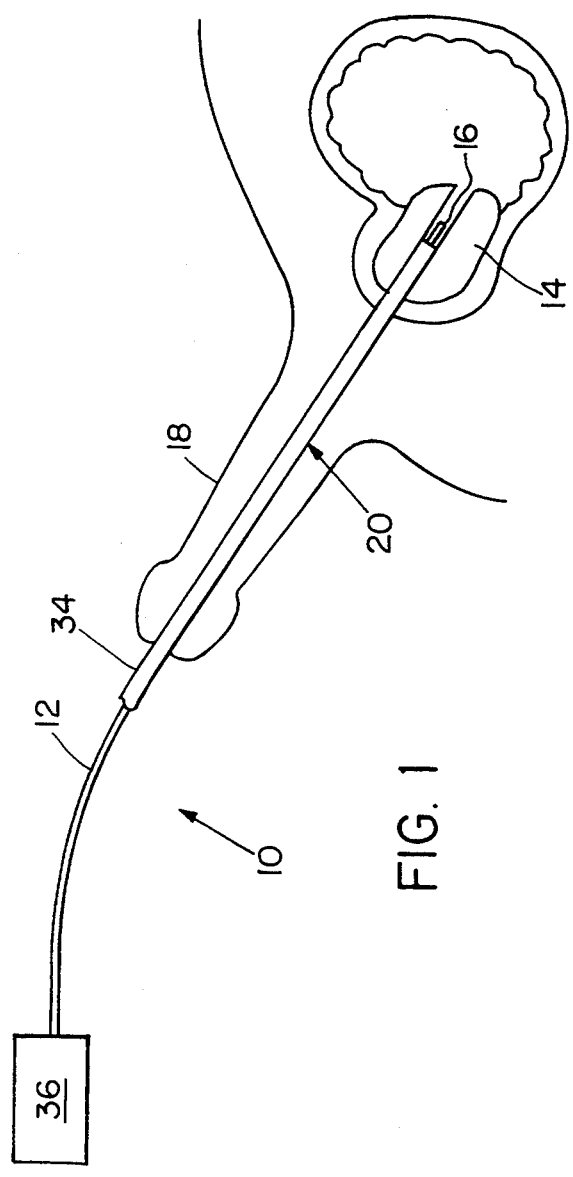
FIG. 1 is a simplified side view of the present invention endoscopic light delivery system.

In FIG. 1, endoscopic light delivery system 10 includes a laser source 36 for generating light which is optically coupled to fiber optics 12. Fiber optics 12 conveys light generated by laser source 36. Fiber optics 12 passes through endoscopic sheath 34 which includes viewing optics (not shown) for enabling the surgeon to view surgical areas. Typically, fiber optics 12 is a single optical fiber having a diameter ranging between 1 mm and 1.5 mm. Alternatively, fiber optics 12 can be a bundle of two or more optical fibers. A light delivery tip generally indicated at 16 is optically coupled to the end of fiber optics 12 and extends from sheath 34 to deliver the light 28 (FIG. 2) conveyed by fiber optics 12 to desired surgical areas. Light delivery tip 16 can be a tip for primarily cutting tissue, primarily coagulating tissue or both.

In order to perform prostate surgery, endoscopic sheath 34 is inserted into the urethra 20 of the penis 18 such that a light delivery tip 16 primarily for coagulating tissue is positioned within prostate gland 14. Endoscopic sheath 34 and light delivery tip 16 are maneuvered within prostate gland 14 to coagulate prostate gland tissue so that bleeding does not occur when the tissue is cut. A second light delivery tip primarily for cutting tissue is then employed to cut away tissue of the prostate gland in order to enlarge the passageway through prostate gland 14. The tissue is cut away in small pieces so that the pieces can be passed during urination. As a result, the surgeon's vision of the surgical area through the endoscope does not become impaired due to bleeding. Alternatively, the prostate tissue can be cut first and then later coagulated.

Figure 2:
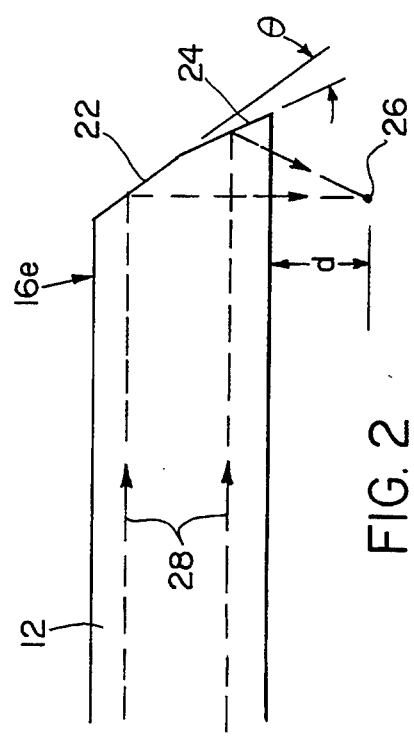
FIG. 2 is a side view of a preferred light delivery tip for the present invention endoscopic light delivery system.

In FIGS. 2–9, various preferred embodiments for light delivery tip 16 are depicted. In FIG. 2, light delivery tip 16e is a tip primarily for cutting tissue. Light delivery tip 16e is formed by polishing the end of fiber optics 12 along two planes 22 and 24 which are angled with respect to each other by an angle $\theta$. Planes 22 and 24 are coated with a reflective coating so that planes 22 and 24 form a reflecting and focusing surface. The reflective coating can be multi-layered so that multiple wavelengths of light can be reflected. Planes 22 and 24 reflect and laterally redirect light 28 conveyed by fiber optics 12 in a lateral direction such that light 28 is focused at a focal point 26. In the drawing, only two rays are shown. All rays do not focus to the same point by this piece-wise linear focusing mirror. However, all rays merge over a small region to increase the laser intensity in that region. By directing light 28 laterally with respect to fiber optics 12, light delivery tip 16e can be easily maneuvered to cut tissue within prostate gland 14.

The angle $\theta$ between planes 22 and 24 preferably ranges between 10° to 20°. By varying the angle $\theta$ between planes 22 and 24, the distance "d" between focal point 26 and optical fiber 12 can be varied. Alternatively, the angle $\theta$ can be of other suitable angles. Additionally, more than two planes can be formed for reflecting and focusing light.

Figure 3:
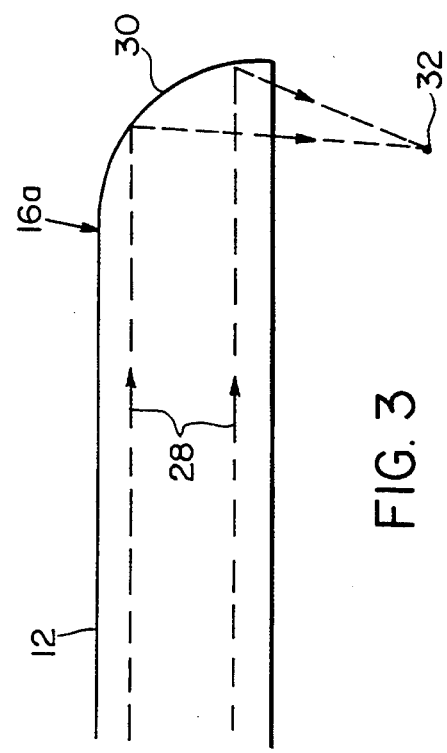
FIG. 3 is a side view of another preferred light delivery tip.

Referring to FIG. 3, light delivery tip 16a is another preferred light delivery tip primarily for cutting tissue which can be substituted for tip 16e. Tip 16a is similar to tip 16e differing in that tip 16a has a curved reflective surface 30 for laterally focusing light 28 conveyed by fiber optics 12 to a focal point 32. This shape of the tip provides better focusing but is more difficult to fabricate. Surface 30 is preferably spherical but alternatively can be parabolic in shape.

In FIGS. 4 and 5A, light delivery tip 16c is another preferred light delivery tip primarily for cutting tissue. Fiber optics 12 is optically coupled to a tip member 50. Tip member 50 is fan shaped along one plane and curved or arch-shaped along another plane. The tip member 50 preferably has a radius of about 5 mm. However, the radius of tip member 50 can be varied depending upon the application. Tip member 50 directs the light 28 conveyed along fiber optics 12 out of an end 52 into a diverging arch-shaped profile 54. The arched profile of light 54 allows delivery tip 16c to be pushed forward to cut small pieces of tissue from prostate gland 14. In the preferred embodiment, the width "w" of tip member 50 is about 5 milimeters wide at end 52. Alternatively, the width "w" of tip member 50 can be of other suitable widths. Additionally, tip member 50 does not have to be fan shaped along one plane.

In FIG. 5B, light delivery tip 16f is another preferred light delivery tip for cutting tissue and is similar to the light delivery tip 16c depicted in FIGS. 4 and 5A. Light delivery tip 16f differs from tip 16c in that tip member 51 is semicircular in shape along one plane and fan shaped along another plane. As a result, tip member 51 directs light out of end 53 into a semicircular or half moon profile 55.

In FIGS. 6 and 7, light delivery tip 16d is another preferred light delivery tip for cutting tissue and is similar to the light delivery tip 16c depicted in FIGS. 4 and 5A. Light delivery tip 16d differs from tip 16c in that tip 16d has multiple optical fibers 60 conveying light through tip member 62. At end 64 of tip member 62, optical fibers 60 are arranged in a fan shaped arch or curve. Optionally, light 28 can be delivered to optical fibers 60 by a single optical fiber 12 optically coupled to optical fibers 60. Additionally, optical fibers 60 can be arranged into a semicircular shape at end 64 to direct light into a semicircular or half-moon profile.

Although the light delivery tips depicted in FIGS. 2–7 have been described for primarily cutting tissue, the tips can also be employed to coagulate tissue.

In FIGS. 8 and 9, delivery tip 16b is another preferred light delivery tip which is used principally for coagulating tissue. Light delivery tip 16b redirects light 28 laterally in multiple directions.

Light delivery tip 16b includes a mirror 44 which is positioned proximate to the end of optical fiber 12. Mirror 44 is held in position with respect to optical fiber 12 by an outer sheath 42. Optical windows 46 and 48 comprising holes in sheath 42 or optically clear material allows light 28 reflected by mirror 44 to exit.

In the preferred embodiment, mirror 44 has at least two reflective facets 44a and 44b, respectively. Additionally, mirror 44 can include more than two facets. Furthermore, mirror 44 can be a conical mirror for directing light laterally in all directions (360°). A spacer 40 is employed to maintain optical fiber 12 in a fixed position with respect to sheath 42 and mirror 44, but spacer 40 can be omitted. Although light delivery tip 16b is used primarily for coagulating tissue, light delivery tip 16b can also be employed for cutting tissue.

FIG. 10 depicts another preferred embodiment of the present invention for simultaneously cutting and coagulating tissue. Endoscopic light delivery system 100 includes laser sources 36a, 36b and 36c for generating light which are optically coupled to optical fibers 12a, 12b and 12c respectively. Laser source 36a generates light having a wavelength suitable for cutting tissue, laser source 36b generates light having a wavelength suitable for coagulating tissue, and laser source 36c generates light having a wavelength suitable for targeting tissue. Fiber optics 12a conveys light generated by laser source 36a, fiber optics 12b conveys light generated by laser source 36b and fiber optics 12c conveys light generated by laser source 36c. Fiber optics 12a, 12b and 12c are optically coupled to fiber optics 12 at junction 13. Fiber optics 12, 12a, 12b and 12c are preferably made of pure silica but can be alternatively made of other suitable materials.

In the preferred embodiment, fiber optics 12 is capable of simultaneously conveying light generated by laser sources 36a, 36b and 36c. As a result, tissue targeted by light generated by laser source 36c can be simultaneously cut and coagulated by light generated by laser sources 36a and 36b. Alternatively, light generated by laser sources 36a, 36b and 36c does not have to be conveyed by fiber optics 12 simultaneously but can be conveyed sequentially.

In order to perform prostate surgery, endoscopic sheath 34 is inserted into the urethra 20 of the penis 18 such that the light delivery tip 116 is positioned within prostate gland 14. Endoscopic sheath 34 and light delivery tip 116 are maneuvered within prostate gland 14 to target and cut away tissue from the prostate gland. Light generated by laser source 36c is positioned on desired tissue with light delivery tip 116 to target the tissue which is to be cut and coagulated. Light generated by laser sources 36a and 36b is then simultaneously delivered to the targeted tissue by light delivery tip 116 to cut and coagulate the tissue. By simultaneously cutting and coagulating tissue, bleeding is minimized. As a result, the surgeon's vision of the surgical area through the endoscope does not become impaired due to bleeding. Any of the tips depicted in FIGS. 2 through 9 can be used with light delivery system 100 for cutting and coagulating tissue.

In order for the light delivery tip 116 to cut as well as coagulate tissue, laser sources 36a and 36b generate light of different wavelengths. Laser source 36a generates light preferably having a wavelength ranging from about 1.4 to 2.1 microns which is a wavelength suitable for cutting tissue. Laser source 36a, for example, can be a Neodymium (Nd YAG) laser that has a 1.44 micron output or a Homium YAG laser which has a 2.1 micron output. Laser source 36b generates light preferably having a wavelength ranging from about 0.8 to 1.1 microns which is a wavelength poorly absorbed by body tissues and hence suitable for coagulating tissue. Laser source 36a, for example, can be a Nd YAG laser which has a 1.064 micron output or a diode laser having a 0.8 to 1 micron output.

Laser source 36c generates light preferably having a wavelength ranging from about 632 nm to 670 nm at a power ranging between 1 to 5 milliwatts. This range of wavelengths and power is suitable for targeting tissue. Laser source 36c, for example, can be a helium neon laser having an output of 632 nm or a diode laser having an output of 670 nm.

Although examples of laser types and wavelengths have been given, laser sources 36a, 36b and 36c do not have to be limited to those specific laser types and wavelength outputs. Additionally, although FIG. 10 shows a single optical fiber 12 conveying light from laser sources 36a, 36b and 36c, separate optical fibers can be employed. Furthermore, fiber optic bundles can also be used. Also, light delivery system 100 can be used in non-endoscopic applications.

Equivalents

While this invention has been particularly shown and described with references to preferred embodiments thereof, it will be understood by those skilled in the art that various changes in form and details may be made therein without departing from the spirit and scope of the invention as defined by the dependent claims.

For example, multiple laser sources can be used for generating light. Additionally, although the present invention has been described for performing prostate surgery, the present invention may be used for performing other types of surgery such as intra-uterine, bladder, urinary track and angioplasty surgery. Furthermore, other types of light delivery tips can be employed such as a plain optical fiber or a globe tipped optical fiber. Finally, various features of the present invention can be used in conjunction with electrocautery surgery.

What is claimed is:

1. An endoscopic light delivery system comprising:
   a laser source for generating light;
   fiber optics having a longitudinal axis optically coupled to the laser source for conveying light generated by the laser; and
   a tip member optically coupled to the fiber optics extending generally axially from the fiber optics, the tip member fanning out from the axis of the fiber optics and being shaped in an arch along a plane perpendicular to the axis of the fiber optics to direct the conveyed light into an arch-shaped profile extending generally axially from the fiber optics.

2. The endoscopic light delivery system of claim 1 in which the tip member is semicircular in shape to direct the conveyed light into a semicircular profile.

3. The endoscopic delivery system of claim 1 further comprising more than one optical fiber for conveying light.

4. The endoscopic delivery system of claim 3 further comprising more than one laser source for generating light.

5. The endoscopic delivery system of claim 1 further comprising:
   a first laser source for generating light of a first wavelength for cutting tissue; and
   a second laser source for generating light of a second wavelength for coagulating tissue.

6. The laser light delivery system of claim 5 further comprising a third laser source optically coupled to the fiber optics for generating light of a third wavelength for targeting tissue.

7. The laser light delivery system of claim 5 in which the first laser source generates light having a wavelength ranging from about 1.4 to 2.1 microns and the second laser source generates light having a wavelength ranging from about 0.8 to 1.1 microns.

8. A method of delivering light with an endoscope comprising the steps of:
   generating light with a laser source;
   conveying light generated by the laser with fiber optics optically coupled to the laser source, the fiber optics having a longitudinal axis; and
   directing the light conveyed by the fiber optics with a tip member optically coupled to the fiber optics which extends generally axially from the fiber optics, the tip member fanning out from the axis of the fiber optics and being shaped in an arch along a plane perpendicular to the axis of the fiber optics to direct the conveyed light into an arch-shaped profile extending generally axially from the fiber optics.

9. The method of claim 8 in which the light is directed into a semicircular profile.

10. The method of claim 8 further comprising the step of conveying the light with more than one optical fiber.

11. The method of claim 10 in which laser light is generated by more than one laser source.

12. The method of claim 8 further comprising the steps of:

generating light of a first wavelength with a first laser source for cutting tissue; and
generating light of a second wavelength with a second laser source for coagulating tissue.

13. The method of claim 12 further comprising the step of generating light of a third wavelength with a third laser source for targeting tissue, the third laser being optically coupled to the fiber optics.

14. The method of claim 8 further comprising the steps of:

generating light having a wavelength ranging from about 1.4 to 2.1 microns with a first laser source; and
generating light having a wavelength ranging from about 0.8 to 1.1 microns with a second laser source.

15. The method of claim 8 in which the light is conveyed by fiber optics made of pure silica material.

* * * * *